United States Patent [19]

Tustin et al.

[11] Patent Number: 5,679,870
[45] Date of Patent: Oct. 21, 1997

[54] PREPARATION OF ACETALDEHYDE

[75] Inventors: Gerald Charles Tustin; Leslie Sharon Depew, both of Kingsport, Tenn.

[73] Assignee: Eastman Chemical Company, Kingsport, Tenn.

[21] Appl. No.: 619,385

[22] Filed: Mar. 21, 1996

[51] Int. Cl.[6] .................................................. C07C 45/00
[52] U.S. Cl. .................................... 568/489; 568/484
[58] Field of Search ............................... 568/489, 484

[56] References Cited

U.S. PATENT DOCUMENTS 4,351,964  9/1982  Nakamura et al. ..................... 568/484

OTHER PUBLICATIONS

Grootendorst et al; Journal of catalysis; 148, 261–269, 1994.
Pestman et al; Recl. Trav. Chim. Pays–Bas; 113; 426–430, 1994.

Akira et al., in *Organometallics*, 4, 1463–1464 (1985).

Carr et al., in *J. Chem. Phys.*, 49, 846–852 (1968).

White et al., in *J. Am. Chem. Soc*, 111, 1185–1193 (1989).

White et al., in *J. Phys. Chem.*, 92, 4111–4119 (1988).

White et al., in *J. Phys. Chem.*, 92, 4120–4127 (1988).

*Surface Science*, 183, 377–402 (1987).

*Surface Science*, 183, 403–426 (1987).

*Primary Examiner*—C. Warren Ivy
*Assistant Examiner*—Sreeni Padmanabhan
*Attorney, Agent, or Firm*—Michael J. Blake; J. Frederick Thomsen; Harry J. Gwinnell

[57] ABSTRACT

Disclosed is a process for the preparation of acetaldehyde by the hydrogenation of ketene in the presence of a transition metal hydrogenation catalyst.

9 Claims, No Drawings

PREPARATION OF ACETALDEHYDE

The Government of the United States of America has rights in this invention pursuant to Cooperative Agreement No. DE-FC22-95PC93052 awarded by the U.S. Department of Energy.

This invention pertains to a process for the preparation of acetaldehyde by the hydrogenation of ketene in the presence of a transition metal hydrogenation catalyst.

Acetaldehyde is an important industrial chemical which has been used commercially in the manufacture of acetic acid, acetic anhydride, cellulose acetate, other acetate esters, vinyl acetate resins, synthetic pyridine derivatives, terephthalic acid, peracetic acid and pentaerythritol. Historically, some of the acetaldehyde use has been associated with the production of acetic acid, but improvements in technology have resulted in more economical acetic acid production from synthesis gas (a mixture of carbon monoxide and hydrogen). This development implies that it may be more economically attractive to produce acetaldehyde from acetic acid rather than to produce acetic acid from acetaldehyde if a technically viable route existed. One objective of the present invention is to provide a means to produce acetaldehyde efficiently from acetic acid.

Acetaldehyde has been produced commercially by the reaction of ethanol with air at 480° C. in the presence of a silver catalyst. This process has been replaced by the Wacker oxidation of ethylene which is more direct and efficient than the ethanol oxidation route. Both the ethanol and the Wacker processes start with ethylene. Acetaldehyde also has been produced by the hydration of acetylene using mercury salts as a catalyst. It is apparent that the handling of mercury poses both environmental and safety problems. The use of acetylene also poses safety concerns, and the high cost of acetylene relative to ethylene has rendered this process obsolete. Acetaldehyde also can be produced by reacting synthesis gas over a rhodium on silica catalyst at elevated temperature and pressure, but the selectivity to acetaldehyde is poor. Acetaldehyde also has been produced from the reaction of methanol with synthesis gas at elevated temperature and pressure using a cobalt iodide catalyst with a group 15 promoter. Neither the rhodium- nor cobalt iodide-catalyzed process has been practiced commercially. Although the Wacker process is the preferred commercial process at this time, it also has many undesirable aspects. These include the special safety and handling problems associated with reacting ethylene with oxygen and the very corrosive nature of the aqueous, acidic chloride-containing reaction mixtures which necessitates very expensive materials of construction. Thus, a need exists for an acetaldehyde synthesis that is an improvement over the existing known processes.

A potentially attractive means to synthesize acetaldehyde is by the hydrogenation of acetic acid. However, the selective hydrogenation of acetic acid is difficult. The reaction is not favored thermodynamically and, therefore, high temperatures and excessive amounts of hydrogen are required. When these conditions are used, selectivity is poor, and byproducts include acetone, carbon dioxide, formaldehyde, ethanol and methane. The acetaldehyde product initially produced is often more reactive than the starting acetic acid frequently resulting in the over reduction to ethanol.

Carr et al., in *J. Chem. Phys.*, 49, 846–852 (1968), teach that the reaction of ketene with hydrogen atoms produces mainly methane and carbon monoxide. White et al., in *J. Am. Chem. Soc*, 111, 1185–1193 (1989), *J. Phys. Chem.*, 92, 4111–4119 (1988), *J. Phys. Chem.*, 92, 4120–4127 (1988), *Surface Science*, 183, 377–402 (1987), and *Surface Science*, 183, 403–426 (1987), describe the interaction of ketene with metal surfaces (Ru and Pt) as studied by spectroscopic techniques. Although adsorbed acetaldehyde can be observed in some cases, it either decomposes or polymerizes on the catalyst. No free acetaldehyde is produced. The desorbed products from these reactions are generally methane or higher hydrocarbons and carbon monoxide.

Ponec et al., in *J. Catal.*, 148, 261–269 (1994) and *Recl. Tray. Chim. Pays-Bas*, 113, 426–430 (1994) describe a high temperature (350° C.) hydrogenation of acetic acid over reduced iron oxide catalysts. Addition of platinum enhances the selectivity to acetaldehyde somewhat. Ketene was identified as a byproduct and possible intermediate. Under conditions where the selectivity to acetaldehyde is good (87–97%), the yield of acetaldehyde is poor (6% or less) even though the reactions are run in a large excess of hydrogen (hydrogen:ketene ratio=60:1). Operation in this mode is impractical from a industrial viewpoint owing to the dilute product stream, extensive recycle and large temperature extremes required to isolate the product. Lower acetaldehyde selectivity (16–40%) is observed at higher yields (13–40%) over a tin oxide catalyst. Byproducts of the reaction include acetone along with smaller amounts of methane and carbon dioxide. Platinum metal (one of the active metals of the present invention) by itself produced no acetaldehyde in the acetic acid hydrogenation reaction, and the only products observed were methane, water, carbon monoxide and carbon dioxide.

A number of ketene-metal complexes have been described in the literature. Shapley et al., in *J. Am. Chem. Soc.*, 108, 508–510 (1986), describe a ruthenium-based ketene complex that does not react with hydrogen. Miyashita et al., in *Organometallics*, 4, 1463–1464 (1985), describe a platinum-based ketene complex that produces a mixture of acetaldehyde, ethanol and hydrocarbons when treated with hydrogen. Geoffroy, et al., in *J. Am. Chem. Soc.*, 106, 4783–4789 (1984) describe an osmium cluster-based ketene complex which decomposes in the presence of hydrogen to form several other osmium clusters, acetic acid and acetaldehyde. None of these metal complex materials are catalytic in their reaction with hydrogen, and only the complex described by Miyashita et al. was prepared from ketene.

The present invention provides an efficient means for the production acetaldehyde from ketene under very mild conditions. The process can be used in combination with known ketene-manufacturing processes to convert a variety of acetyl and related compounds such as acetic acid, acetic anhydride, diketene, and acetone to acetaldehyde. The process of the present invention comprises the preparation of acetaldehyde by the steps of (1) contacting hydrogen and ketene gases with a catalyst comprising a metal selected from the elements of Groups 9 and 10 (IUPAC classification; Group 9=Co, Rh and Ir; Group 10=Ni, Pd and Pt) of the periodic table in a hydrogenation zone and (2) recovering acetaldehyde from the hydrogenation zone. Our novel process does not involve the formation of ketene-metal complexes of the kind described in the literature discussed hereinabove.

The process may be operated at temperatures in the range of from about 0° and 250° C. although low temperatures give low reaction rates and excessively high temperatures cause accelerated degradation of the ketene resulting in yield loss. Thus, a more preferred range of temperatures is between about 50° and 200° C. The most preferred temperature range is between about 70° and 150° C.

The catalytic hydrogenation process may be carried out at pressures ranging from about 0.05 to about 100 bars absolute (pressures given herein are bars absolute). However, excessively high pressures increase the possibility of the formation of ketene polymerization products whereas excessively low pressures cause lower reaction rates and it is difficult to remove the heat from the reaction. The process preferably is carried out at a pressure of from about 0.1 to about 20 bars with the most preferred range being from about 0.25 to 10 bars. Because ketene is normally generated and used at a pressure of about one bar pressure or less, the hydrogenation most conveniently is carried out at a pressure of about one bar or less.

The reactant mixture can consist essentially of 100% ketene and hydrogen or a nonreactive (inert) diluent gas such as nitrogen, argon, helium or light hydrocarbon may be added. For example, the presence of a nonreactive gas in the reactant mixture can assist with the removal of heat from the reaction zone. When used, inert diluents can comprise from about 1 to about 95 volume percent of the reactant feed. The use of excessive amounts of diluent gas reduce the rate of the reaction and make the isolation of the product acetaldehyde more difficult. The presence of significant amounts of carbon monoxide can adversely affect the hydrogenation catalysts, especially the preferred palladium catalysts. Therefore, the reactant mixture normally should contain less than about 1 volume percent carbon monoxide, preferably less than 1000 ppm carbon monoxide.

The mole ratio of hydrogen to ketene may vary considerably, and may range from about 0.25:1 to 10:1. The hydrogen:ketene mole ratio preferably is in the range of about 1:1 to 8:1, most preferably, about 2:1 to 4:1. Hydrogen:ketene mole ratios below 1:1 limit the conversion of ketene and lower the rate of reaction. Although the rate of the reaction increases with increasing hydrogen:ketene ratios, excessive amounts of hydrogen increase the difficulty encountered in isolating the product. Also, the use of excessively large amounts of hydrogen in combination with low space velocity can result in the production of some ethanol or ethyl acetate after most of the ketene has been consumed. Ethanol normally is not produced in the process of the invention, but ethyl acetate is detectable at higher conversions.

The metals which catalyze the hydrogenation of ketene to acetaldehyde according to the present invention may be found in what was formally termed group VIII or group VIIIA of the periodic table of the elements and, more specifically, what currently is termed groups 9 and 10 of the periodic table of the elements. The catalyst preferably is selected from rhodium, platinum and, especially, palladium. The catalytic metals may be used in the form of unsupported metals or they can be used in the form of a supported catalyst comprising the catalytic metal deposited on a catalyst support material. Alumina, carbon, titanium dioxide, silica, barium sulfate, barium carbonate and calcium carbonate are examples of suitable support materials. The Lindlar catalyst (palladium on calcium carbonate modified with lead) also is effective for the reaction but is not as selective as palladium on the other supports mentioned above. When a support is used, the metal loading may range from about 0.1 to about 10 weight percent. Metal loadings outside these ranges also perform the reaction but in general do not optimize the use of the metal and support. It is often preferable to use an unsupported palladium catalyst, such as palladium sponge, because hydrogen treatment often restores activity more effectively than it does with a supported catalyst. It also may be possible to employ the catalytically-active metals in the form of salts or complexes which are soluble in a liquid reaction medium in which the process may be carried out.

Various modes of operation can be utilized in the practice of the process of the invention. For example, the process may be utilized as a heterogeneous, vapor phase process wherein a vapor (gas) comprising ketene, hydrogen and, optionally, a nonreactive diluent gas is fed to a reaction (hydrogenation) zone containing one or more beds of the above-described catalysts. An alternative heterogeneous mode of operation consists of a vapor/liquid/solid phase process wherein a feed gas comprising ketene, hydrogen and, optionally, a nonreactive diluent gas is fed to a reaction zone containing the catalyst as a finely divided suspension in a nonreactive liquid reaction medium such as mineral oil. The product acetaldehyde may be removed from the reaction zone by gas stripping. In another embodiment of the vapor/liquid/solid phase method of operation, a mixture of the gas feed and a nonreactive liquid can be fed to a hydrogenation zone where it is passed over the solid catalyst in a trickle bed mode of operation. Finally, the process may be practiced using a homogeneous catalyst solution consisting of a salt or complex of the catalytically-effective metal dissolved in a nonreactive, liquid reaction medium (solvent) to which the gas mixture comprising ketene, hydrogen and, optionally, a nonreactive diluent gas is fed. Such homogeneous operation is not preferred.

The process of the invention can be operated as a batch, semi-continuous or continuous process. The most efficient operation of the hydrogenation process is achieved by operating the process continuously in a heterogeneous, gas phase mode of operation. In this preferred method of operation, the process of the invention provides for the continuous production of acetaldehyde by the steps of:

(1) continuously feeding a vapor (gas) comprising ketene, hydrogen and, optionally, a nonreactive diluent gas to a reaction (hydrogenation) zone containing one or more beds of the catalytically-effective, hydrogenation catalyst; and (2) continuously removing a product gas comprising acetaldehyde from the reaction zone.

The catalysts used in the preferred heterogeneous, continuous process comprise supported and unsupported palladium catalysts.

The gas hourly space velocity (GHSV-volumes of reactant per volume of catalyst per hour) of the ketene-containing reactant and diluent gases feed can range from about 10 to 100,000 using the preferred heterogeneous mode of operation. The GHSV preferably is in the range of about 100 to 50,000, and most preferably, it is in the range of about 1000 to about 20,000. In general an increase in the GHSV increases the rate of reaction but decreases the conversion. The selection of the optimum GHSV depends on the physical form of the catalyst and the rate and conversion desired.

The process of the present invention is further illustrated by the following examples. In the apparatus utilized in the examples, metered gas flows were provided by four Tylan Model FC-260 mass flow controllers. Electric temperature control and monitoring were provided by a Dow Camile® control system interfaced with a Gateway Model 2000 486DX/33 computer. Tygon® tubing was used for ketene-free gases, and PharMed® tubing was used for ketene-containing gases. Condensers, the cyclone assembly, all traps, reactors and scrubbers were constructed of glass or quartz. Metered gases were fed through 4 gas lines L1 through L4 and each gas line was teed to a pressure relief column containing water to prevent accidental over pressurization. Ketene was generated for laboratory use by the method described by Fisher et al. in *J. Org. Chem.*, 18, 1055–1057 (1953) by the pyrolysis of acetic anhydride with minor modifications. Although acetic acid pyrolysis is the preferred industrial route to ketene, it is generally not practical on a laboratory scale. Any source of ketene can be used provided it is substantially free of catalyst inhibitors or poisons. Acetic anhydride was fed at 600 mL per hour using a Harvard Apparatus Model 22 syringe infusion pump. The acetic anhydride was fed to the top of a 107 cm long by 25 mm outside diameter (O.D.) vertical, quartz vaporizer/pyrolysis tube along with 25 standard cubic centimeters per minute (SCCM) helium. The vaporizer/pyrolysis tube was indented at a distance of 27 cm from the top and contained a 9 mm O.D. quartz thermocouple well extending about two thirds the length of the reactor from top towards the bottom. The portion of the vaporizer/pyrolysis tube extending 22 cm up from the indentations also contained quartz chips and was heated with heating tape controlled at 200° C. The lower section of the vaporizer/pyrolysis tube was heated by a Lindberg three element electric furnace controlled at 520° C. The quenching condenser below the vaporizer/pyrolysis tube was held at about −55° C. by circulating methanol cooled in a solid carbon dioxide/acetone bath.

The mixture from the quenching condenser passed through two identical cyclones measuring 16 mm O.D. at the top and 80 mm from the top of the cyclone body to the bottom of the tapered section. The inlet and outlet lines of the cyclone were 2 mm inside diameter (I.D.), and the liquid from the bottom of the cyclone assembly was drained into a 500 ml flask. The gas displacement tube (10 mm O.D.) connecting the drain flask to the cyclone assembly was bent to provide a liquid seal. The misted vapor from the ketene generator cyclone assembly was passed through two demisting traps held at 0° C. to a three-way stopcock (SC1) via the ketene generator line. In one position, SC1 vented excess ketene-containing vapors from the ketene generator line to a water scrubber. In another position, SC1 sent the ketene-containing vapors to the ketene inlet line of a trap/vaporizer assembly. The trap/vaporizer assembly was a modified two-piece 32×200 mm vacuum trap having the bottom portion of the trap narrowed to 19 mm O.D. and extending an additional 100 mm. A 7 mm O.D./2 mm I.D. gas inlet tube extended along the outer body of the trap/vaporizer assembly and was connected to the base of the extended tube section. The gas inlet tube was connected to a metered nitrogen line containing a stopcock (SC2). The ketene inlet line was the normal 10 mm O.D. tube found in the standard vacuum trap design. The ketene outlet line was the normal 10 mm O.D. side tube found in the standard vacuum trap design. The trap/vaporizer assembly was loaded with about 30 ml liquid ketene by immersing the assembly in a −78° C. bath with SC2 closed and SC1 opened to the trap/vaporizer while the ketene generator was operating. During the procedure of loading the trap/vaporizer with ketene, the trap/vaporizer outlet line was isolated from the reactor and accessed to the water scrubber via stopcocks SC3, SC4 and SC5. The three-way stopcock SC3 connected the trap/vaporizer outlet line to the hydrogenation reactor inlet line or to the reactor bypass line. Three-way stopcock SC4 connected the reactor outlet and the bypass line to a line leading to three-way stopcock SC5. SC5 directed the gas stream from the reactor or bypass line to a general purpose water scrubber used to destroy ketene before venting or to an analytical scrubber containing circulating methanol. Helium (normally set for 50 SCCM) was always flowing through line L2 and mixing with any material exiting the outlet line of the trap/vaporizer both during the ketene generation procedure and during the hydrogenation procedure. About 15 minutes of ketene generator operation were required to fill the tapered portion of the trap/vaporizer.

After the ketene trap/vaporizer was loaded, it was isolated from the ketene generator by turning SC1 to divert the vapors from the ketene generator line to the water scrubber. Stopcock SC2 was opened and nitrogen (normal rate 88 SCCM) was metered through the liquid ketene held at −78° C. These conditions transpired the ketene from the trap/vaporizer at a rate of 1 mmol/minute (about 22.4 SCCM). Hydrogen (normal rate 44.8 SCCM) was metered through L1 to the temperature-controlled reactor. Details of the type of reactor used and reaction conditions are provided in the specific examples. The hydrogenation reaction was begun by turning SC3 to feed the ketene/nitrogen gas mixture to the hydrogenation reactor inlet line to which hydrogen was also fed. Initially, the product vapor was vented to the water scrubber through SC4 and SC5. For vapor phase reactions, a two-necked, 100-mL, round bottomed flask was connected to the base of the reactor to trap any material that was not volatile at ambient temperature. To collect a sample for analysis, SC5 was turned to send the product vapors to an analytical scrubber containing methanol (100 mL). The methanol scrubber mixture was circulated by a Masterflex peristaltic pump. Any unreacted ketene was converted to methyl acetate in the methanol scrubber. Acetaldehyde existed in the methanol as free acetaldehyde and acetaldehyde dimethyl acetal. A condenser containing solid carbon dioxide and acetone was fitted to the top of the scrubber to prevent material loss. After a set period of time, the product vapor stream was again diverted to the water scrubber via SC5, and the methanol solution was drained from the scrubber base via drain stopcock SC6 and weighed. The scrubber was then replenished with fresh methanol for the subsequent sample.

Products contained in the methanol scrubber solution were analyzed by gas chromatography using a Hewlett Packard Model 5890 gas chromatograph fitted with a 30 m×0.25 mm FFAP capillary column (0.25 micron film thickness) programmed at 35° C. for 7 minutes, 15° C./minute to 220° C. and holding at 220° C. for 2 minutes using a flame ionization detector held at 280° C. (injector temperature=240° C). Mixtures were prepared for gas chromatographic analysis by adding 5 mL of a tetrahydrofuran solution containing 2% decane internal standard to an accurately weighed 1 g sample of the methanol scrubber solution.

The following definitions apply to the specific examples:

---

Gas Hourly Space Velocity (GHSV) = volumes of gas,
i.e., the total volume of the ketene + hydrogen +
diluent gases, per volume of catalyst per hour
under reaction conditions.
Space Time Yield (STY) = grams of acetaldehyde
produced per liter of catalyst per hour.
% Conversion (Conv) = 100(mmoles ketene
reacted)/(mmoles ketene fed),
% Ketene Accountability (Acct) = 100(mmoles ketene
recovered + mmoles acetaldehyde
produced)/(mmoles ketene fed),
% Acetaldehyde Selectivity (Select) = 100(mmoles
acetaldehyde produced)/(mmoles ketene
reacted).

---

GHSV is based on the total volume of all gases, i.e., ketene, hydrogen and diluent gases, fed to the hydrogenation reactor. The volume of any noncatalytic solid (vapor phase operation) or liquid (vapor/liquid/solid operation) material added to the reactor as a diluent is not included in the GHSV or STY calculations. The accountability calculations are calculated on the basis of the above-described routine gas chromatographic analysis performed which could detect methyl acetate, acetaldehyde, dimethyl acetal and ethanol.

Methane, carbon monoxide, diketene, ketene oligomerization products, ethylene and ethyl acetate have been detected but not quantified as byproducts, particularly in the early stages of evaluation of catalysts of high activity. Other material losses resulted from absorption of material into the porous tubing used to connect the various parts of the reaction apparatus.

EXAMPLE 1

This example illustrates the use of a 5% palladium on barium sulfate catalyst for the selective production of acetaldehyde from ketene and hydrogen using a steam heated reactor for temperature control. The glass reactor used in this example consisted of a 53 cm by 25 mm O.D. tube fitted with a permanent thermowell extending from the base of the reactor. The central portion of the reactor tube was constructed with a condenser jacket which was in turn enclosed in a vacuum jacket to prevent heat loss. The length of the jacketed portion was 37 cm. The 25 mm O.D. tube had indentations 6 cm above the base of the jacket to support the catalyst bed.

The reactor was loaded to a distance extending 25 mm above the indentations with quartz wool covered with 8×16 mesh quartz chips. A physical mixture was made from 5% Pd on barium sulfate powder (1.0015 g=0.9 ml) and 8×16 mesh quartz chips (50 ml), and this mixture was loaded above the quartz chips covering the quartz wool. The catalyst bed length was 15 cm. An additional charge of 4×8 mesh quartz chips was loaded on top of the catalyst bed to increase the height of the packed bed an additional 8 cm up to the top of the condenser jacket.

Hydrogen was fed to the reactor at 44.8 SCCM and one atmosphere pressure, and the reactor was heated with steam to 97° C. The temperature along the entire length of the catalyst bed was constant to within 0.5° C. The catalyst was treated with hydrogen in this manner for 22 hours, and then a mixture of ketene (1 mmol/minute), nitrogen (88 SCCM) and helium (50 SCCM) was added to the hydrogen stream entering the reactor. The temperature of the catalyst bed remained constant at 97°–98° C. during the hydrogenation reaction. Samples were taken throughout the day, and at the end of the day, the ketene, nitrogen and helium was diverted from the reactor to the water scrubber, and the reactor was allowed to remain at 97°–98° C. with hydrogen flowing at 10 SCCM overnight to restore activity to the catalyst. The ketene was allowed to evaporate from the trap/vaporizer, which was then cleaned to prepare it for the next day's operation. The reactor was operated in this manner for 4 days.

The following samples were taken at the total time on stream (TTOS) indicated in minutes that both hydrogen and ketene were contacting the catalyst, and samples were collected over 60 or 90 minute periods:

| Sample | TTOS, min. |
| --- | --- |
| 1-A | 286–376 |
| 1-B | 641–731 |
| 1-C | 739–799 |
| 1-D | 994–1084 |
| 1-E | 1097–1157 |
| 1-F | 1362–1452 |

Overnight hydrogen treatments of the catalyst were performed after the TTOS was 376, 731 and 1084 minutes. The gas hourly space velocity used and the space time yield, ketene conversion, ketene accountability and acetaldehyde selectivity achieved for each period of reaction time over which Samples 1-A–1-F were collected are shown below.

| Sample | GHSV | STY | Conv | Acct | Select |
| --- | --- | --- | --- | --- | --- |
| 1-A | 18600 | 1420 | 78 | 70 | 61 |
| 1-B | 18600 | 1440 | 70 | 79 | 70 |
| 1-C | 18600 | 1680 | 100 | 57 | 57 |
| 1-D | 18600 | 1500 | 66 | 85 | 78 |
| 1-E | 18600 | 1600 | 65 | 90 | 84 |
| 1-F | 18600 | 1370 | 72 | 75 | 65 |

The differences in results with time reflect the effects of natural catalyst aging and the elapsed time following overnight hydrogen treatments.

EXAMPLE 2

This example illustrates the use of a Pd on barium carbonate catalyst instead of the Pd on barium sulfate catalyst used in example 1. A physical mixture was prepared from 5% Pd on barium carbonate powder (1.0075 g=0.91 mL) and quartz chips as described in Example 1. The same reactor, reactor loading sequence, hydrogen pretreatment, flow and temperature settings were used as per Example 1. The following samples were taken at the total time on stream (TTOS) indicated in minutes that both hydrogen and ketene were contacting the catalyst and samples were collected over 60 or 90 minute periods:

| Sample | TTOS, min. |
| --- | --- |
| 2-A | 286–376 |
| 2-B | 380–440 |
| 2-C | 635–725 |
| 2-D | 729–789 |
| 2-E | 984–1074 |
| 2-F | 1350–1440 |

Overnight hydrogen treatments of the catalyst were performed after the TTOS was 376, 725 and 1074 minutes. The gas hourly space velocity used and the space time yield, ketene conversion, ketene accountability and acetaldehyde selectivity achieved for each period of reaction time over which Samples 2A–2F were collected are shown below.

| Sample | GHSV | STY | Conv | Acct | Select |
| --- | --- | --- | --- | --- | --- |
| 2-A | 18400 | 1390 | 67 | 81 | 72 |
| 2-B | 18400 | 1550 | 62 | 92 | 87 |
| 2-C | 18400 | 1230 | 57 | 85 | 74 |
| 2-D | 18400 | 1480 | 56 | 95 | 92 |
| 2-E | 18600 | 1310 | 53 | 92 | 86 |
| 2-F | 18400 | 1240 | 56 | 86 | 76 |

The differences in the results obtained over a period of time reflect the effects of natural catalyst aging and the elapsed time following overnight hydrogen treatments.

EXAMPLE 3

This example illustrates the use of a Pd on calcium carbonate catalyst. A physical mixture was prepared from 5% Pd on calcium carbonate powder (1.0028 g=1.4 mL) and quartz chips as described in Example 1. The same reactor, reactor loading sequence, hydrogen pretreatment, flow and temperature settings were used as in Example 1. The following samples were taken at the total time on stream (TTOS) indicated in minutes that both hydrogen and ketene were contacting the catalyst and samples were collected over 60 or 90 minute periods.

| Sample | TTOS, min. |
|---|---|
| 3-A | 195–285 |
| 3-B | 573–663 |
| 3-C | 955–1045 |
| 3-D | 1146–1206 |
| 3-E | 1411–1501 |

Overnight hydrogen treatments of the catalyst were performed after TTOS times of 380, 758 and 1140 minutes. The gas hourly space velocity used and the space time yield, ketene conversion, ketene accountability and acetaldehyde selectivity achieved for each period of reaction time over which Samples 3A–3E were collected are shown below.

| Sample | GHSV | STY | Conv | Acct | Select |
|---|---|---|---|---|---|
| 3-A | 12000 | 1210 | 82 | 81 | 78 |
| 3-B | 12000 | 1070 | 85 | 72 | 67 |
| 3-C | 12000 | 1020 | 82 | 71 | 65 |
| 3-D | 12000 | 1220 | 100 | 65 | 65 |
| 3-E | 12000 | 1080 | 100 | 57 | 57 |

The differences in the results achieved over the periods of time reflect the effects of natural catalyst aging and the elapsed time following overnight hydrogen treatments.

EXAMPLE 4

This example illustrates the use of a lead-modified Pd on calcium carbonate catalyst (Lindlar catalyst) and can be compared to Example 3 to illustrate the effect of lead modification on the performance of the catalyst. A physical mixture was prepared from lead-modified 5% Pd on calcium carbonate powder (1.0048 g=1.2 mL) and quartz chips as described in Example 1. The same reactor, reactor loading sequence, hydrogen pretreatment, flow and temperature settings were used as in Example 1. The following samples were taken at the total time on stream (TTOS) indicated in minutes that both hydrogen and ketene were contacting the catalyst and samples were collected over 60 or 90 minute periods.

| Sample | TTOS, min. |
|---|---|
| 4-A | 188–278 |
| 4-B | 561–651 |
| 4-C | 929–1019 |
| 4-D | 1122–1182 |
| 4-E | 1382–1472 |

Overnight hydrogen treatments of the catalyst were performed after TTOS times of 373, 746 and 1114 minutes. The gas hourly space velocity used and the space time yield, ketene conversion, ketene accountability and acetaldehyde selectivity achieved for each period of reaction time over which Samples 4A–4E were collected are shown below.

| Sample | GHSV | STY | Conv | Acct | Select |
|---|---|---|---|---|---|
| 4-A | 13900 | 760 | 77 | 57 | 45 |
| 4-B | 13900 | 740 | 71 | 62 | 47 |
| 4-C | 13900 | 630 | 66 | 63 | 44 |
| 4-D | 13900 | 680 | 100 | 31 | 31 |
| 4-E | 13900 | 605 | 62 | 65 | 44 |

The differences in performance with time reflect the effects of natural catalyst aging and the elapsed time following overnight hydrogen treatments.

EXAMPLE 5

This example illustrates the use of a Pd on alumina catalyst in a long term experiment in which the total time on stream exceeded 100 hours. A physical mixture was prepared from 1% Pd on alumina, 2 mm sized pellets (5.0186 g=6 ml), and quartz chips as described in Example 1. The same reactor, reactor loading sequence, hydrogen pretreatment, and reaction conditions were used as in Example 1. Although reaction conditions were varied during this extended experiment (refer to Examples 6, 7 and 8 below), the data presented in this example were obtained under the flow and temperature settings reported in Example 1. The following samples were taken at the total time on stream (TTOS) indicated in minutes that both hydrogen and ketene were contacting the catalyst, and samples were collected over 60 or 90 minute periods:

| Sample | TTOS, min. |
|---|---|
| 5-A | 260–350 |
| 5-B | 641–731 |
| 5-C | 1051–1141 |
| 5-D | 2363–2423 |
| 5-E | 2618–2708 |
| 5-F | 6762–6822 |

Overnight hydrogen treatments of the catalyst were performed after TTOS times of 350, 731, 1141, 1563, 1971, 2350, 2708, 3116, 3514, 3918, 4311, 4702, 5086, 5464, 5915, 6294 and 6754 minutes. The gas hourly space velocity used and the space time yield, ketene conversion, ketene accountability and acetaldehyde selectivity achieved for each period of reaction time over which Samples 5A–5F were collected are shown below.

| Sample | GHSV | STY | Conv | Acct | Select |
|---|---|---|---|---|---|
| 5-A | 2800 | 190 | 59 | 84 | 72 |
| 5-B | 2800 | 150 | 50 | 84 | 69 |
| 5-C | 2790 | 120 | 43 | 84 | 62 |
| 5-D | 2790 | 140 | 34 | 96 | 89 |
| 5-E | 2790 | 110 | 27 | 99 | 96 |
| 5-F | 2790 | 90 | 25 | 94 | 78 |

The differences in performance with time reflect the effects of natural catalyst aging and the elapsed time following overnight hydrogen treatments.

EXAMPLE 6

This example illustrates the effect of reaction temperature on the rate of acetaldehyde production using the Pd on alumina catalyst and procedure described in Example 5. The steam heating system was replaced with a temperature-controlled circulating water bath for data obtained below 90° C. The data were obtained at a point in the catalyst history where changes in activity due to catalyst deactivation were minimal. Flow settings were the same as those used in the previous examples. The following samples were taken at the total time on stream (TTOS) indicated in minutes that both hydrogen and ketene were contacting the catalyst, and samples were collected over 90 minute periods. The temperature values given below are the temperatures in °C. of the catalyst bed.

| Sample | TTOS, min. | Temperature |
| --- | --- | --- |
| 6-A | 5374–5464 | 98.0 |
| 6-B | 5730–5830 | 88.4 |
| 6-C | 6204–6294 | 77.8 |
| 6-D | 5550–5640 | 69.8 |
| 6-E | 5986–6076 | 59.3 |
| 6-F | 6394–6484 | 49.4 |

Overnight hydrogen treatments of the catalyst were performed as described in Example 5. The gas hourly space velocity used and the space time yield, ketene conversion, ketene accountability and acetaldehyde selectivity achieved for each period of reaction time over which Samples 5A–5F were collected are shown below.

| Sample | GHSV | STY | Conv | Acct | Select |
| --- | --- | --- | --- | --- | --- |
| 6-A | 2790 | 91 | 32 | 89 | 65 |
| 6-B | 2720 | 62 | 34 | 80 | 41 |
| 6-C | 2640 | 41 | 30 | 80 | 31 |
| 6-D | 2580 | 41 | 28 | 82 | 33 |
| 6-E | 2500 | 24 | 13 | 92 | 41 |
| 6-F | 2420 | 15 | 12 | 91 | 29 |

EXAMPLE 7

This example illustrates the effect of altering the amounts of hydrogen and ketene on the rate of acetaldehyde production using the procedure and Pd on alumina catalyst described in Example 5. The data were obtained at a point in the catalyst history where changes in activity due to catalyst deactivation were minimal. The temperature of the catalyst was maintained at 98° C. and the space velocity was held essentially constant by changing the amount of diluent helium when other gas flows were changed. A different space velocity was used for the study of varying hydrogen levels than was used for the study for varying ketene levels. A more dilute gas stream was used when the ketene levels were varied. The following samples were taken at the total time on stream (TTOS) indicated in minutes that both hydrogen and ketene were contacting the catalyst, and samples were collected over 60 or 90 minute periods. The values given for the ketene and hydrogen feed rates are mmols per minute.

| Sample | TTOS, min. | Ketene Feed Rate | Hydrogen Feed Rate |
| --- | --- | --- | --- |
| 7-A | 3703–3793 | 1.0 | 0.5 |
| 7-B | 3583–3673 | 1.0 | 1.0 |
| 7-C | 1563–1473 | 1.0 | 2.0 |
| 7-D | 1215–1305 | 1.0 | 3.0 |
| 7-E | 1348–1438 | 1.0 | 4.0 |
| 7-F | 3986–4076 | 0.5 | 4.0 |
| 7-G | 4382–4472 | 1.0 | 4.0 |
| 7-H | 4771–4861 | 1.5 | 4.0 |
| 7-I | 5249–5339 | 2.0 | 4.0 |

Overnight hydrogen treatments of the catalyst were performed as described in Example 5. The gas hourly space velocity used and the space time yield, ketene conversion, ketene accountability and acetaldehyde selectivity achieved for each period of reaction time over which Samples 7A–7I were collected are shown below.

| Sample | GHSV | STY | Conv | Acct | Select |
| --- | --- | --- | --- | --- | --- |
| 7-A | 2800 | 59 | 23 | 91 | 59 |
| 7-B | 2800 | 77 | 37 | 80 | 47 |
| 7-C | 2800 | 128 | 47 | 83 | 622 |
| 7-D | 2800 | 165 | 51 | 87 | 74 |
| 7-E | 2800 | 172 | 49 | 90 | 80 |
| 7-F | 4300 | 77 | 46 | 90 | 77 |
| 7-G | 4300 | 110 | 36 | 89 | 70 |
| 7-H | 4300 | 109 | 33 | 84 | 50 |
| 7-I | 4300 | 131 | 34 | 81 | 43 |

EXAMPLE 8

This example illustrates the effect of altering the gas hourly space velocity (GHSV) of the hydrogen and ketene feed on the rate of acetaldehyde production using the procedure and Pd on alumina catalyst described in Example 5. The data were obtained at a point in the catalyst history where changes in activity due to catalyst deactivation were minimal. The temperature of the catalyst was maintained at 98° C., and the gas ratios were the same as those employed in Examples 1 and 5. The following samples were taken at the total time on stream (TTOS) indicated in minutes that both hydrogen and ketene were contacting the catalyst, and samples were collected over 60 or 90 minute periods:

| Sample | TTOS, min. |
| --- | --- |
| 8-A | 1631–1721 |
| 8-B | 1473–1563 |
| 8-C | 1756–1846 |
| 8-D | 1975–2035 |

Overnight hydrogen treatments of the catalyst were performed as described in Example 5. The gas hourly space velocity used and the space time yield, ketene conversion, ketene accountability and acetaldehyde selectivity achieved for each period of reaction time over which Samples 8A–8D were collected are shown below.

| Sample | GHSV | STY | Conv | Acct | Select |
| --- | --- | --- | --- | --- | --- |
| 8-A | 1400 | 106 | 49 | 99 | 99 |
| 8-B | 2800 | 128 | 47 | 82 | 62 |
| 8-C | 3700 | 153 | 37 | 87 | 63 |
| 8-D | 4910 | 185 | 34 | 87 | 62 |

EXAMPLE 9

This example illustrates the use of a Pd on carbon catalyst. A physical mixture was prepared from 5% Pd on carbon powder (1.0026 g=2.6 mL) and quartz chips as described in Example 1. The same reactor, reactor loading sequence, hydrogen pretreatment, flow and temperature settings were used as in Example 1. The following samples were taken at the total time on stream (TTOS) indicated in minutes that both hydrogen and ketene were contacting the catalyst, and samples were collected over 60 or 90 minute periods:

| Sample | TTOS, min. |
|---|---|
| 9-A | 336–426 |
| 9-B | 435–495 |
| 9-C | 710–800 |
| 9-D | 1294–1384 |
| 9-E | 1484–1574 |

Overnight hydrogen treatments of the catalyst were performed after TTOS times of 426, 800 and 1214 minutes. The gas hourly space velocity used and the space time yield, ketene conversion, ketene accountability and acetaldehyde selectivity achieved for each period of reaction time over which Samples 9A–9E were collected are shown below.

| Sample | GHSV | STY | Conv | Acct | Select |
|---|---|---|---|---|---|
| 9-A | 6420 | 585 | 100 | 58 | 58 |
| 9-B | 6420 | 663 | 100 | 65 | 65 |
| 9-C | 6420 | 607 | 100 | 60 | 60 |
| 9-D | 6420 | 589 | 100 | 58 | 58 |
| 9-E | 6420 | 552 | 81 | 74 | 67 |

The differences in performance with time reflect the effects of natural catalyst aging and the elapsed time following overnight hydrogen treatments.

EXAMPLE 10

This example illustrates the use of a Pd on titanium dioxide catalyst. A physical mixture was prepared from 1% Pd on titanium dioxide powder (5.001 g=6 mL) and quartz chips as described in Example 1. The same reactor, reactor loading sequence, hydrogen pretreatment, flow and temperature settings were used as per example 1. The following samples were taken at the total time on stream (TTOS) indicated in minutes that both hydrogen and ketene were contacting the catalyst, and samples were collected over 90 minute periods:

| Sample | TTOS, min. |
|---|---|
| 10-A | 262–352 |
| 10-B | 615–705 |
| 10-C | 775–865 |
| 10-D | 1318–1408 |

Overnight hydrogen treatments of the catalyst were performed after TTOS times of 352, 705 and 1055 minutes. The gas hourly space velocity used and the space time yield, ketene conversion, ketene accountability and acetaldehyde selectivity achieved for each period of reaction time over which Samples 10A–10D were collected are shown below.

| Sample | GHSV | STY | Conv | Acct | Select |
|---|---|---|---|---|---|
| 10-A | 2800 | 108 | 36 | 89 | 68 |
| 10-B | 2800 | 112 | 42 | 83 | 61 |
| 10-C | 2800 | 100 | 61 | 61 | 37 |
| 10-D | 2800 | 108 | 49 | 76 | 51 |

EXAMPLE 11

This example illustrates the use of a bulk, support-free Pd catalyst. A physical mixture was prepared from palladium sponge powder (1.005 g=0.4 mL) and quartz chips as described in Example 1. The same reactor, reactor loading sequence, hydrogen pretreatment, flow and temperature settings were used as in Example 1. The following samples were taken at the total time on stream (TTOS) indicated in minutes that both hydrogen and ketene were contacting the catalyst, and samples were collected over 90 minute periods:

| Sample | TTOS, min. |
|---|---|
| 11-A | 429–519 |
| 11-B | 784–874 |
| 11-C | 1138–1228 |

Overnight hydrogen treatments were performed after TTOS times of 354, 709 and 1064 minutes. The gas hourly space velocity used and the space time yield, ketene conversion, ketene accountability and acetaldehyde selectivity achieved for each period of reaction time over which Samples 11A–11C were collected are shown below.

| Sample | GHSV | STY | Conv | Acct | Select |
|---|---|---|---|---|---|
| 11-A | 41800 | 1310 | 24 | 96 | 84 |
| 11-B | 41800 | 1290 | 24 | 95 | 80 |
| 11-C | 41800 | 1310 | 20 | 100 | 100 |

EXAMPLE 12

This example illustrates the use of a Rh on alumina catalyst. The reactor tube used in this example was a 25 mm O.D. quartz tube containing an internal quartz thermocouple. The reactor had indentations near the base. The reactor was loaded with quartz chips measuring 12 cm high from the indentations. The catalyst, 0.5% Rh on 3mm alumina pellets (5.016 g=5.1 mL), was added. An additional layer of quartz chips measuring 6 cm high was placed on top of the catalyst bed. The reactor was placed in a single element electric furnace having a 23 cm long heated zone such that the catalyst was positioned in the center of the heated zone of the furnace. The catalyst was treated overnight with hydrogen (44.8 SCCM) at 200° C. and then allowed to cool to ambient temperature. Ketene (1 mmol/minute), helium (25 SCCM), nitrogen (88 SCCM), and hydrogen (44.8 SCCM) were fed to the reactor, and the furnace was not on. The catalyst bed temperature rose from ambient temperature to 30° C. with the gas hourly space velocity being 2350 and the vapor product was sampled over a 90 minute period. The space time yield of acetaldehyde was 56 at 11% ketene conversion. The ketene accountability and the acetaldehyde selectivity were 100% and 97%, respectively. The activity of this catalyst for acetaldehyde production decreased to zero during the following hour as the catalyst bed temperature dropped to 24° C. The catalyst once again became active for the production of acetaldehyde when the furnace was set for 100° C. with a space velocity of 3250 and the catalyst bed temperature at 146° C. The sample was collected over a 90 minute period, and the space time yield of acetaldehyde was 31 at a ketene conversion 73%. The ketene accountability and the acetaldehyde selectivity were 33% and 8%, respectively.

EXAMPLE 13

This example illustrates the use of a Pt on alumina catalyst. The procedure and reactor used in Example 12 was repeated except that the Rh on alumina catalyst was replaced with 0.5% Pt on 3 mm alumina pellets (5.0 g=6.1 mL). The hydrogen pretreatment and reaction conditions used in Example 12 were also repeated. No acetaldehyde was detected with the furnace at ambient temperature. The furnace was then set for 100° C. The catalyst bed temperature rose to 148° C. with a space velocity of 2700. The sample was collected over a 90 minute period, and the space time yield of acetaldehyde was 45 at 68% ketene conversion. The ketene accountability and the acetaldehyde selectivity were 42% and 15%, respectively.

EXAMPLE 14

This example illustrates the process of the invention operated in the vapor/liquid/solid mode using a gas stripped reactor. The reaction vessel consisted of a glass cylindrical reaction flask having a ground flanged top joint, gas dispersing stirrer and ground flange reactor head fitted with a precision stirrer bearing, thermocouple and gas outlet port. Dimensions of the cylindrical reaction flask were 5 cm inner diameter by 28 cm high. Two bands of 5 equally spaced 5 cm high indentations were located with the bottom of the bands at 6 and 15 cm up from the base of the reactor. The bands of indentations acted as baffles, and the indentations of the two bands were staggered. The gas dispersing stirrer was a hollow 1 cm O.D. glass tube sealed at the top and opened at the bottom and had two bands of stirrer blades located at the bottom of the stirrer and 11 cm up from the bottom. Each band of stirrer blades contained four 1.5×1.5 cm blades, and the blades of the two bands were staggered. The stirrer had a hole in the side which acted as an inlet port for the reactant gases which were introduced through a side arm on the precision stirrer bearing. The reactor was loaded with 5% Pd on barium carbonate powder (1.0480 g=0.94 mL) and dodecane (300 ml). The assembled reactor was heated at 95° C. in a steambath overnight with stirring and with hydrogen (44.8 SCCM) sparging through the slurry. Ketene (1 mmol/minute), helium (50 SCCM), nitrogen (88 SCCM) were then added to the existing hydrogen stream. Products were analyzed from methanol scrubber solutions as in the preceding examples, with the product vapor exiting the gas stripped reactor outlet port contacting the scrubber solution. The slurry temperature remained at 95° C. with a space velocity of 17600 (based on the catalyst volume). The sample was collected over a 60 minute period, and the space time yield of acetaldehyde was 365 (based on the catalyst volume) at 21% ketene conversion. The ketene accountability and the acetaldehyde selectivity were 92% and 62%, respectively.

The invention has been described in detail with particular reference to preferred embodiments thereof, but it will be understood that variations and modifications can be effected within the spirit and scope of the invention.

We claim:

1. Process for the preparation of acetaldehyde by the steps comprising (1) contacting hydrogen and ketene gases with a catalyst comprising a metal selected from the elements of Groups 9 and 10 of the periodic table in a hydrogenation zone at a temperature of 50° to 200° C. and (2) recovering acetaldehyde from the hydrogenation zone.

2. Process according to claim 1 wherein the contacting is carried out at a pressure of 0.1 to 20 bars absolute.

3. Process according to claim 2 wherein a nonreactive diluent gas also is fed to the hydrogenation zone.

4. Process according to claim 2 wherein the catalyst is a palladium catalyst.

5. Process according to claim 4 wherein the temperature is about 70° to 150° C., the pressure is about 0.25 to 10 bars absolute and the catalyst is a supported or unsupported palladium catalyst.

6. Continuous process for the production of acetaldehyde by the steps of:

(1) continuously feeding a gas comprising ketene, hydrogen and, optionally, a nonreactive diluent gas to a hydrogenation zone at temperature of 50° to 200° C. containing one or more beds of a catalytically-effective, hydrogenation catalyst comprising a metal selected from the elements of Groups 9 and 10 of the periodic table; and (2) continuously removing a product gas comprising acetaldehyde from the reaction zone.

7. Process according to claim 6 wherein the hydrogenation zone is at a temperature of about 70° to 150° C. and a pressure of about 0.25 to 10 bars absolute and the catalyst is a supported or unsupported palladium catalyst.

8. Continuous process for the production of acetaldehyde by the steps of:

(1) continuously feeding a gas comprising ketene, hydrogen and, optionally, a nonreactive diluent gas to a hydrogenation zone at a temperature of 50° to 200° C. containing a catalytically-effective, hydrogenation catalyst comprising a metal selected from the elements of Groups 9 and 10 of the periodic table in the presence of an inert liquid reaction medium; and (2) continuously removing a product gas comprising acetaldehyde from the reaction zone.

9. Process according to claim 8 wherein the temperature is about 70° to 150° C., the pressure is about 0.25 to 10 bars absolute and the catalyst is a supported or unsupported palladium catalyst.

* * * * *